(12) United States Patent
Lochead et al.

(10) Patent No.: US 6,248,757 B1
(45) Date of Patent: Jun. 19, 2001

(54) 3-(PYRROLIDIN-3-YL)-1,3,4-OXADIAZOL-2(3H)-ONE DERIVATIVES AND THEIR USE AS 5-HT4 LIGANDS

(75) Inventors: Alistair Lochead, Charenton; Samir Jegham, Argenteuil; Jean Jeunesse, Champigny sur Marne, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/403,779

(22) PCT Filed: May 4, 1998

(86) PCT No.: PCT/FR98/00887

§ 371 Date: Nov. 4, 1999

§ 102(e) Date: Nov. 4, 1999

(87) PCT Pub. No.: WO98/50381

PCT Pub. Date: Nov. 12, 1998

(30) Foreign Application Priority Data

May 6, 1997 (FR) .................................................. 97 05539

(51) Int. Cl.[7] ........................ A61K 31/445; A61K 31/41; C07D 413/06; C07D 271/10
(52) U.S. Cl. ...................... 514/326; 514/364; 546/209; 548/144
(58) Field of Search .......................... 548/144; 514/364, 514/326; 546/209

(56) References Cited

U.S. PATENT DOCUMENTS 5,525,619 * 6/1996 Koenig et al. ................. 514/364

FOREIGN PATENT DOCUMENTS

WO93/16072 8/1993 (WO).
WO95/32965 12/1995 (WO).
WO97/17345 5/1997 (WO).

* cited by examiner

Primary Examiner—Floyd D. Higel
Assistant Examiner—Ebenezer Sackey
(74) Attorney, Agent, or Firm—Jacobson, Price, Holman & Stern, PLLC

(57) ABSTRACT

Compounds corresponding to the general formula (I)

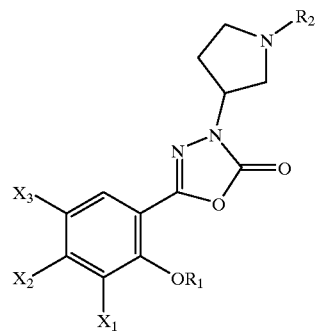

in which $R_1$ represents hydrogen or an alkyl or cycloalkylmethyl group, $X_1$ represents hydrogen or a halogen or an alkoxy group, or alternatively $OR_1$ and $X_1$ together represent a group of formula $-OCH_2O-$, $-O(CH_2)_2-$, $-O(CH_2)_3-$, $-O(CH_2)_2O-$ or $-O(CH_2)_3O-$, $X_2$ represents hydrogen, an amino group or a group of general formula $-NHCO_2R$ in which R represents an alkyl or phenylalkyl group, $X_3$ represents hydrogen or a halogen, and $R_2$ represents hydrogen or an alkyl, phenylalkyl or [(4-dimethylamino)piperid-1-ylcarbonyl]alkyl group. Therapeutic application.

5 Claims, No Drawings

3-(PYRROLIDIN-3-YL)-1,3,4-OXADIAZOL-2 (3H)-ONE DERIVATIVES AND THEIR USE AS 5-HT4 LIGANDS

This application is a 371 of PCT/FR98/00887 filed May 4, 1998.

The present invention relates to compounds of the general formula (I)

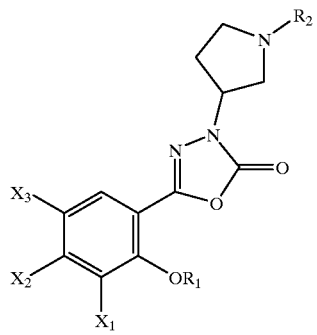

in which $R_1$ represents a hydrogen atom or a $(C_1-C_4)$alkyl or cyclo $(C_3-C_7)$alkylmethyl group, $X_1$ represents a hydrogen atom or a $(C_1-C_4)$alkoxy group, or alternatively $OR_1$ and $X_1$ together represent a group of formula —OCH$_2$O—, —O(CH$_2$)$_2$—, —O(CH$_2$)$_3$—, —O(CH$_2$)$_2$O— or —O(CH$_2$)$_3$O—, $X_2$ represents a hydrogen atom, an amino group or a group of general formula —NHCO$_2$R in which R represents a $(C_1-C_4)$alkyl or phenyl$(C_1-C_2)$alkyl group, $X_3$ represents a hydrogen or halogen atom, and $R_2$ represents a hydrogen atom or a $(C_1-C_6)$alkyl group, or a phenyl$(C_1-C_4)$alkyl or [(4-dimethylamino)piperid-1-ylcarbonyl] $(C_2-C_4)$alkyl group.

Since the carbon atom via which the pyrrolidine ring is attached to the rest of the molecule is asymmetric, the compounds of the invention can exist in the form of pure enantiomers or mixtures of enantiomers.

They can also exist in the form of bases or addition salts with acids.

The compounds of general formula (I) can be prepared according to a process illustrated by the scheme which follows.

Scheme

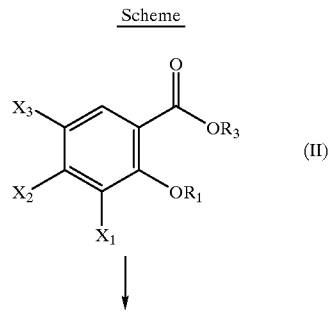

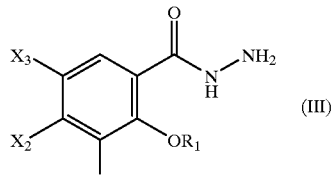

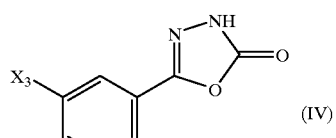

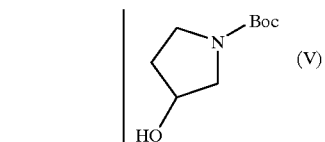

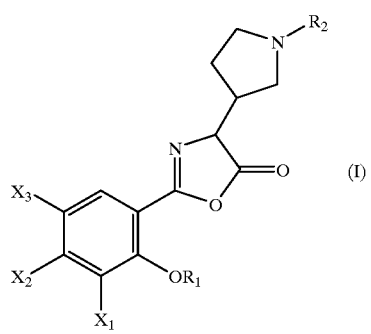

An ester of general formula (II), in which $R_1$, $X_1$, $X_2$ and $X_3$ are as defined above and $R_3$ represents a methyl or ethyl group, is reacted with hydrazine hydrate, in the absence of solvent or in a polar protic solvent, for example ethanol, in order to obtain a hydrazide of general formula (III), which is cyclized into an oxadiazole of general formula (IV) either using phosgene, in an aprotic solvent, for example dioxane, or using phenyl chloroformate, in an aprotic solvent, for example toluene.

When, in the general formula (II), $X_2$ represents an amino group, the latter reacts with the phosgene and the product obtained is esterified with an alcohol of general formula ROH, in which R is defined as above, the amino group thus being protected by a group —CO$_2$R. The oxadiazole of general formula (IV) is then reacted with an alcohol of general formula (V), in which Boc represents a (1,1-dimethylethoxy)carbonyl group, in the presence of triphenylphosphine and ethyl azodicarboxylate, in an aprotic solvent, for example tetrahydrofuran, after which the (1,1-dimethylethoxy) carbonyl protecting group is removed using trifluoroacetic acid. A compound of general formula (I) in which $R_2$ represents a hydrogen atom is thus obtained.

If so desired, the latter compound can then be subjected to an alkylation using a derivative of general formula $R_2$-X, in which X represents a leaving group, for example a halogen atom or a methane-sulphonate or para-toluenesulphonate group, and $R_2$ is as defined above, but other than a hydrogen atom, in the presence of triethylamine, in an aprotic solvent, for example acetonitrile. Finally, when X$_2$ is a group —NHCO$_2$R, the protecting group can, if so desired, be removed in acidic medium.

The starting esters of general formula (II) and/or the corresponding acids are described in particular in patent applications EP-0,231,139, EP-0,234,872, WO-84/03281, WO-93/16072 and WO-94/19344.

The alcohols of general formula (V) are known or can be prepared according to any known method; (R/S)-1-[(1,1-dimethylethoxy)carbonyl]pyrrolidin-3-ol is described in *J. Am. Chem. Soc.* (1982) 104 5852–5853, and the (R) enantiomer is described in *Tetrahedron* (1988) 44 (17) 5479–5486.

The examples which follow illustrate in detail the preparation of a number of compounds according to the invention. The elemental microanalyses and the IR and NMR spectra confirm the structures of the compounds obtained. The compound numbers indicated in parentheses in the titles correspond to those in the table given later. In the compound names, the hyphen "-" forms part of the name, and the line "_" serves merely to indicate the line break; it should be removed in the absence of a line break and should not be replaced either by a normal hyphen or by a space.

EXAMPLE 1

(Compound No. 9)
Phenylmethyl [2-chloro-4-(5-oxo-4-(pyrrolidin-3-yl)-4,5-dihydro-1,3,4-oxadiazol-2-yl)-5-methoxyphenyl] carbamate 1.1. 4-Amino-5-chloro-2-methoxybenzoic acid hydrazide 51.5 g (0.239 mol) of methyl 4-amino-5-chloro-2-methoxybenzoate suspended in 460 ml of ethanol are introduced into a 1 l reactor. 119 g (2.39 mol) of hydrazine hydrate are added over 15 min and the mixture is refluxed for 15 h.

The mixture is cooled using a bath of ice and the precipitate is collected by filtration, rinsed with ethanol and dried under reduced pressure at 80° C. for 2 h 30. 47.5 g of product are thus obtained.

Melting point: 211° C.

1.2. Phenylmethyl [2-chloro-5-methoxy-4-(5-oxo-4,5-dihydro-1,3,4-oxadiazol-2-yl)phenyl]carbamate 461 ml (0.875 mol) of a 1.93M solution of phosgene in toluene is added dropwise, over one hour, at room temperature and with stirring, to a suspension of 37.7 g (0.175 mol) of 4-amino-5-chloro-2-methoxybenzoic acid hydrazide in 1200 ml of dioxane in a 3 l reactor.

The mixture is stirred at room temperature overnight and is then heated at 80° C. for 1 h. The excess phosgene is stripped off by passing a stream of argon through at this temperature for 2 h. 72 ml (0.7 mol) of benzyl alcohol are then added and the heating is continued for 1 h at 100° C. The mixture is cooled and concentrated under reduced pressure and the residue is triturated from isopropyl ether. The solid obtained is filtered off and dried. 60.3 g of product are thus obtained.

Melting point: 214° C.

1.3. Phenylmethyl [2-chloro-4-[3-[1-(1,1-dimethyl_ethoxy) carbonyl]pyrrolidin-3-yl]-5-oxo-4,5-dihydro-1,3,4-oxadiazol-2-yl]-5-methoxyphenyl]_carbamate 9.8 g (26.1 mmol) of phenylmethyl [2-chloro-5-methoxy-4-(5-oxo-4,5-dihydro-1,3,4-oxadiazol-2-yl)phenyl]_carbamate dissolved in 100 ml of tetrahydrofuran, 11.6 g (44.3 mmol) of triphenylphosphine and 4.9 g (26.1 mmol) of 1-[(1,1-dimethylethoxy)carbonyl]_pyrrolidin-3-ol are introduced into a 500 ml three-necked round-bottomed flask. While stirring the mixture at 0° C., a solution of 5.9 g (33.9 mmol) of ethyl azodicarboxylate in 6 ml of tetrahydrofuran is added dropwise and the stirring is continued at room temperature for 24 h.

The solvent is evaporated off under reduced pressure and the residue is purified by chromatography on silica gel, eluting with 65/35, 60/40 and finally 30/70 mixtures of heptane and ethyl acetate. 10.1 g of product are obtained.

Melting point: 138° C.

1.4. Phenylmethyl [2-chloro-4-(5-oxo-4-(pyrrolidin-3-yl)-4,5-dihydro-1,3,4-oxadiazol-2-yl)-5-methoxy_phenyl] carbamate 10.1 g (18.5 mmol) of phenylmethyl [2-chloro-4-[3-[1-(1,1-dimethylethoxy)carbonyl]pyrrolidin-3-yl]-5-oxo-4,5-dihydro-1,3,4-oxadiazol-2-yl]-5-methoxy_phenyl] carbamate dissolved in 100 ml of dichloromethane are introduced into a 500 ml three-necked round-bottomed flask. The solution is cooled to 0° C., 14.3 ml (185 mmol) of trifluoroacetic acid are added dropwise and the mixture is stirred at room temperature for 17 h.

The solvent is evaporated off under reduced pressure, the residue is dissolved in 1500 ml of ethanol and the solution is acidified by addition of 4.5 ml of a solution of hydrochloric acid in ethanol. A white solid is obtained, which is taken up in 80 ml of water and 80 ml of chloroform, aqueous ammonia is added and the mixture is extracted with chloroform. The solvent is evaporated off under reduced pressure in order to obtain 4.7 g of product in the form of a white solid.

Melting point: 131° C.

EXAMPLE 2

(Compound No. 10)
Phenylmethyl [2-chloro-5-methoxy-4-[5-oxo-4-(1-butyl_pyrrolidin-3-yl)-4,5-dihydro-1,3,4-oxadiazol-2-yl]_phenyl] carbamate 1.5 g (3.37 mmol) of phenylmethyl [2-chloro-4-(5-oxo-4-(pyrrolidin-3-yl)-4,5-dihydro-1,3,4-oxadiazol-2-yl)-5-methoxyphenyl]carbamate dissolved in 26 ml of acetonitrile, and 1.41 ml (10.1 mmol) of triethylamine are placed in a 100 ml three-necked round-bottomed flask. A solution of 0.6 g (4.38 mmol) of 1-bromobutane in 4 ml of acetonitrile is added and the mixture is heated at 60° C. for 15 h.

The solvent is evaporated off under reduced pressure and the residue is purified by chromatography on silica gel, eluting with a 99/1/0.1, 98/2/0.2 and finally 95/5/0.5 mixture of chloroform, methanol and aqueous ammonia. 1.35 g of product are thus obtained in the form of a white solid.

Melting point: 114° C.

EXAMPLE 3

(Compound No. 8)
5-(4-Amino-5-chloro-2-methoxyphenyl)-3-[3-(1-butyl-pyrrolidin-3-yl)]-1,3,4-oxadiazol-2(3H)-one hydrobromide 1.29 g (2.58 mmol) of phenylmethyl [2-chloro-5-methoxy-4-[5-oxo-4-(1-butylpyrrolidin-3-yl)-4,5-dihydro-1,3,4-oxadiazol- 2-yl]phenyl]carbamate dissolved in 13 ml of acetic acid are introduced into a 50 ml three-necked round-bottomed flask, 3.2 ml of a 33% solution of hydrobromic acid in acetic acid are added and the mixture is stirred at room temperature for 46 h.

The solvent is evaporated off under reduced pressure and the solid obtained is washed with ether and then with ethanol and recrystallized from ethanol in order to obtain 0.53 g of pure product in the form of a white solid.

Melting point: 197° C.

EXAMPLE 4

(Compound No. 11)

Phenylmethyl (S)-[6-chloro-8-[(4-pyrrolidin-3-yl)-5-oxo-4, 5-dihydro-1,3,4-oxadiazol-2-yl]-2,3-dihydro-1,4-benzodioxin-5-yl)carbamate 4.1. Ethyl 8-amino-2,3-dihydro-1,4-benzodioxine-5-carboxylate 23.5 g (0.198 mol) of thionyl chloride are introduced slowly into a 2 l three-necked round-bottomed flask containing 772 ml of ethanol cooled to −40° C., with stirring, the stirring is continued at this temperature for 1 h, 38.6 g (0.198 mol) of 8-amino-2,3-dihydro-1,4-benzodioxine-5-carboxylic acid dissolved in 100 ml of ethanol are added slowly, over 15 min, and the mixture is allowed to warm to room temperature overnight.

The mixture is refluxed for 4 h, the solvent is evaporated off under reduced pressure, the residue is taken up in water and sodium carbonate and the resulting mixture is extracted with chloroform. After washing, drying and evaporation of the organic phase, 34.06 g of ester are obtained in the form of a white solid.

Melting point: 112° C.

4.2. Ethyl 8-amino-7-chloro-2,3-dihydro-1,4-benzodioxine-5-carboxylate 37 g (0.165 mol) of ethyl 8-amino-2,3-dihydro-1,4-benzodioxine-5-carboxylate dissolved in 370 ml of dioxane are introduced into a 1 l round-bottomed flask, 23.2 g (0.174 mol) of N-chlorosuccinimide are added, at room temperature and with magnetic stirring, and the mixture is stirred overnight. It is diluted with water, extracted with ethyl acetate and, after the usual processing of the organic phase, 42 g of compound are obtained, which product is recrystallized from a mixture of diethyl ether and diisopropyl ether.

Melting point: 105–106° C.

4.3. 8-Amino-7-chloro-2,3-dihydro-1,4-benzodioxine-5-carboxylic acid hydrazide 38.4 g (0.149 mol) of ethyl 8-amino-7-chloro-2,3-dihydro-1,4-benzodioxine-5-carboxylate suspended in 150 ml of ethanol are introduced into a 1 l reactor, 149 g (2.98 mol) of hydrazine hydrate are added, over 15 min, and the mixture is refluxed for 1 h.

The mixture is cooled using a bath of ice and the precipitate is collected by filtration, washed with ethanol and dried under reduced pressure.

33 g of compound are obtained.

Melting point: 227–231° C.

4.4. Phenylmethyl [6-chloro-8-(5-oxo-4,5-dihydro-1,3,4-oxadiazol-2-yl)-2,3-dihydro-1,4-benzodioxin-5-yl]carbamate 32.6 g of 8-amino-7-chloro-2,3-dihydro-1-benzodioxine-5-carboxylic acid hydrazide and 330 ml of dioxane are introduced into a 1 l reactor, at room temperature and with magnetic stirring, 310 ml (0.4 mol) of a 0.193M solution of phosgene in toluene are added dropwise to this suspension over one and a half hours and the mixture is stirred at room temperature overnight and heated at reflux for 5 h.

The excess phosgene is stripped off at this temperature by passing a stream of argon through for 2 h, the mixture is cooled and concentrated under reduced pressure, the residue is taken up in 200 ml of benzyl alcohol and heated to 100° C. overnight, the mixture is cooled and concentrated under reduced pressure and the residue is triturated from diisopropyl ether. After filtration and drying, 52.6 g of compound are obtained.

Melting point: 230° C.

4.5. Phenylmethyl (S)-[6-chloro-8-[4-[1-[(1,1-dimethylethoxy)carbonyl]pyrrolidin-3-yl]-5-oxo-4,5-dihydro-1,3,4-oxadiazol-2-yl]-2,3-dihydro-1,4-benzodioxin-5-yl]carbamate 10.8 g (26.7 mmol) of phenylmethyl [6-chloro-8-(5-oxo-4,5-dihydro-1,3,4-oxadiazol-2-yl)-2,3-dihydro-1,4-benzodioxin-5-yl]carbamate dissolved in 110 ml of tetrahydrofuran, and 11.9 g (45.4 mmol) of triphenyl phosphine are placed in a 500 ml three-necked round-bottomed flask. A solution of 5.0 g (26.7 mmol) of (R)-1-[(1,1-dimethylethoxy)carbonyl]pyrrolidin-3-ol in 50 ml of tetrahydrofuran is added and the solution is cooled to 0° C. A solution of 5.5 ml (34.7 mmol) of ethyl azodicarboxylate in 6 ml of tetrahydrofuran is then added dropwise and stirring is continued for 20 h.

The solvent is evaporated off under reduced pressure and the residue is purified by chromatography on silica gel, eluting with a 99/1 mixture of chloroform and methanol. Fractions containing the product are recovered and are repurified by chromatography on silica gel, eluting with chloroform. 4.8 g of pure product are thus obtained in the form of a white solid.

Melting point: 157° C. $[\alpha]^{20}_D$=+36.8° (c=1, CHCl$_3$)

4.6. Phenylmethyl (S)-[6-chloro-8-[(4-pyrrolidin-3-yl)-5-oxo-4,5-dihydro-1,3,4-oxadiazol-2-yl]-2,3-dihydro-1,4-benzodioxin-5-yl)carbamate 4.7 g (8.2 mmol) of phenylmethyl (S)-[6-chloro-8-[4-[1-[(1,1-dimethylethoxy)carbonyl]pyrrolidin-3-yl]-5-oxo-4,5-dihydro-1,3,4-oxadiazol-2-yl]-2,3-dihydro-1,4-benzodioxin-5-yl)carbamate dissolved in 47 ml of dichloromethane are introduced into a 250 ml three-necked round-bottomed flask. The solution is cooled to 0° C., 6.3 ml (82.0 mmol) of trifluoroacetic acid are added and the mixture is stirred at room temperature for 4 h.

The solvent is evaporated off under reduced pressure and 40 ml of water and 40 ml of chloroform are added. The solution is basified by addition of 4 ml of concentrated aqueous ammonia, it is extracted with dichloromethane and the organic phase is evaporated off under reduced pressure. The residue is purified by chromatography on silica gel, eluting with a 95/5/0.5 mixture of chloroform, methanol and aqueous ammonia, in order to obtain 3.5 g of product in the form of a white solid.

Melting point: 126° C. $[\alpha]^{20}_D$=3,00 (c=1, CHCl$_3$).

EXAMPLE 5

(Compound No. 3).

(S)-5-(8-amino-7-chloro-2,3-dihydro-1,4-benzodioxin-5-yl)-3-[1-[5-[4-(dimethylamino)piperidin-1-yl]-5-oxopentyl]pyrrolidin-3-yl]-1,3,4-oxadiazol-2-(3H)-one 5.1. Methyl (S)-3-[5-[7-chloro-8-[[(phenylmethoxy)carbonyl]amino]-2,3-dihydro-1,4-benzodioxin- 5-yl]2-oxo-2,3-dihydro-1,3,4-oxadiazol-3-yl]-pyrrolidine-1-pentanoate 3.46 g (7.32 mmol) of phenylmethyl (S)-[6-chloro-8-[(4-pyrrolidin-3-yl)-5-oxo-4,5-dihydro-1,3,4-oxadiazol-2-yl]-2,3-dihydro-1,4-benzodioxin-5-yl)carbamate dissolved in 62 ml of acetonitrile, and 6.2 g (44 mmol) of triethylamine are introduced into a 250 ml three-necked round-bottomed flask. 2.74 g (19 mmol) of methyl 5-chloropentanoate dissolved in 7 ml of acetonitrile are added at room temperature and the reaction medium is refluxed for 120 h. The solvent is evaporated off under reduced pressure, the residue is taken up in 70 ml of water and 70 ml of chloroform, the organic phase is separated out, the solvent is evaporated off under reduced pressure and the liquid residue is purified by chromatography on silica gel, eluting with a 98/2/0.2 mixture of chloroform, methanol and aqueous ammonia. 0.54 g of product is thus obtained in the form of a sticky paste.

$[\alpha]^{20}_D$=+29.20 (c=1, CHCl$_3$)

5.2. (S)-3-[5-[8-amino-7-chloro-2,3-dihydro-1,4-benzodioxin-5-yl]2-oxo-2,3-dihydro-1,3,4-oxadiazol-3-yl] pyrrolidine-1-pentanoic acid 0.50 g (0.85 mmol) of methyl (S)-3-[5-[7-chloro-8-[[(phenylmethoxy)carbonyl]amino]-2,3-dihydro-1,4- benzodioxin-5-yl]2-oxo-2,3-dihydro-1,3,4-oxadiazol-3-yl]pyrrolidine-l-pentanoate dissolved in 5 ml of concentrated aqueous hydrochloric acid is placed in a 25 ml round-bottomed flask and the reaction medium is refluxed for 22 h.

$[\alpha]^{20}_D = +26°$ (c=0.4, CHCl$_3$).

The table which follows illustrates the chemical structures and the physical properties of a number of compounds of the invention.

TABLE

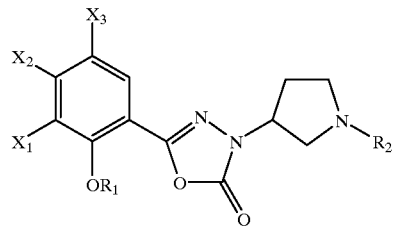

(I)

| *No. | OR$_1$ | x$_1$ | x$_2$ | x$_3$ | R$_2$ | Conf. | Salt | m.p. (° C.) | $[\alpha]_D^{20}$ |
|---|---|---|---|---|---|---|---|---|---|
| 1 | —O(CH$_2$)$_2$O— | | NH$_2$ | Cl | —(CH$_2$)$_2$C$_6$H$_5$ | R/S | HCl | 219 | — |
| 2 | —O(CH$_2$)$_2$O— | | NH$_2$ | Cl | (CH$_2$)$_4$CONC$_5$H$_9$N(CH$_3$)$_2$ | R/S | HCl | 148–150 | — |
| 3 | —O(CH$_2$)$_2$O— | | NH$_2$ | Cl | (CH$_2$)$_4$CONC$_5$H$_9$N(CH$_3$)$_2$ | S | — | paste | +26 (c = 0.4, CH$_2$Cl$_2$) |
| 4 | —O(CH$_2$)$_2$O— | | NH$_2$ | Cl | —(CH$_2$)$_3$CH$_3$ | R/S | HBr | 218–221 | — |
| 5 | —O(CH$_2$)$_2$O— | | NH$_2$ | Cl | —CH(CH$_3$)$_2$ | R/S | HBr | 250 | — |
| 6 | —O(CH$_2$)$_2$O— | | NH$_2$ | Cl | (CH$_2$)$_3$CONC$_5$H$_9$N(CH$_3$)$_2$ | R/S | 2ox. | 145–150 | — |
| 7 | OCH$_3$ | H | NH$_2$ | Cl | —(CH$_2$)$_2$C$_6$H$_5$ | R/S | HBr | 200–204 | — |
| 8 | OCH$_3$ | H | NH$_2$ | Cl | —(CH$_2$)$_3$CH$_3$ | R/S | HBr | 197 | — |
| 9 | OCH$_3$ | H | NHCO$_2$CH$_2$C$_6$H$_5$ | Cl | H | R/S | — | 131 | — |
| 10 | OCH$_3$ | H | NHCO$_2$CH$_2$C$_6$H$_5$ | Cl | —(CH$_2$)$_3$CH$_3$ | R/S | — | 114 | — |
| 11 | —O(CH$_2$)$_2$O— | | NHCO$_2$CH$_2$C$_6$H$_5$ | Cl | H | S | — | 126 | -3.0 (c = 1, CHCl$_3$) |

*In the "R$_2$" column, "NC$_5$H$_9$N(CH$_3$)$_2$" denotes a 4-(dimethylamino)piperid-1-yl group.
In the "Salt" column, "—" denotes a compound in base form, "HCl" denotes a hydrochloride, "HBr" denotes a hydrobromide and "2ox." denotes a dioxalate.
*amendment according to A.34

The aqueous hydrochloric acid is evaporated off under reduced pressure, in order to obtain 0.25 g of crude product which is used without further purification in the following step.

5.3. (S)-5-(8-amino-7-chloro-2,3-dihydro-1,4-benzodioxin-5-yl)-3-[1-[5-[4-(dimethyl_amino)piperidin-1-yl]-5-oxopentyl]pyrrolidin-3-yl]-1,3,4-oxadiazol-2-(3H)-one 0.24 g (0.51 mmol) of (S)-3-[5-[7-chloro-8-amino-2,3-dihydro-1,4-benzodioxin-5-yl]2-oxo-2,3-dihydro-1,3,4-oxadiazol-3-yl]pyrrolidine-1-pentanoic acid dissolved in 2.5 ml of dimethylformamide, and 0.14 ml (1.01 mmol) of triethylamine are introduced into a 25 ml three-necked round-bottomed flask. A solution of 0.16 g (1.01 mmol) of 1,1'-carbonylbis-1H-imidazole in 1.1 ml of dimethylformamide is added dropwise and the mixture is stirred at room temperature for 2 h 30 min. A solution of 0.76 mmol of 4-(dimethylamino)piperidine in 1.8 ml of dimethylformamide (prepared beforehand by heating a suspension of 0.16 g (0.76 mmol) of 4-(dimethylamino)piperidine dihydrochloride in 1.8 ml of dimethylformamide and 0.28 ml (2.02 mmol) of triethylamine at 60° C. for 2 h) is added and the mixture is stirred at room temperature for 18 h.

The reaction medium is poured into 30 ml of water and extracted with chloroform. The product is purified by chromatography on silica gel, eluting with a 95/5/0.5 and then 80/20/2 mixture of chloroform, methanol and aqueous ammonia. 0.08 g of product is thus obtained in the form of a sticky paste.

The compounds of the invention underwent tests which revealed their value as therapeutically active substances.

Thus, the compounds of the invention were studied as regards their affinity towards the 5-HT$_4$ receptors in guinea pig striatum according to the method described by Grossman et al. in Br. J. Pharmacol. (1993) 109 618–624.

Guinea pigs (Hartley, Charles River, France) weighing 300 to 400 g are sacrificed, the brains are removed and the striata are excised and frozen at −80° C.

On the day of the experiment, the tissue is thawed to +4° C. in 33 volumes of Hepes-NaOH buffer (50 mM, pH 7.4 at 20° C.), the mixture is homogenized using a Polytron™ grinder, the homogenate is centrifuged at 48,000×g for 10 min, the pellet is recovered, resuspended and recentrifuged under the same conditions and the final pellet is suspended in Hepes-NaOH buffer, in a proportion of 30 mg of tissue per ml. 100 µl of this membrane suspension is incubated at 0° C. for 120 min in the presence of [$^3$H]GR113808 (ligand described in the article cited, specific activity 80–85 Ci/mmol) in a final volume of 1 ml of Hepes-NaOH buffer (50 mM, pH=7.4), in the presence or absence of test compound. The incubation is stopped by filtration through a Whatman GF/B filter pretreated with 0.1% polyethyleneimine, each tube is rinsed with 4 ml of buffer at 0° C., the filtration is repeated and the radioactivity retained on the filter is measured by liquid scintigraphy.

The non-specific binding is determined in the presence of 30 µM serotonin. The specific binding represents 90% of the total radioactivity recovered on the filter.

For each concentration of test compound, the percentage of inhibition of the specific binding of [$^3$H]GR113808, and then the IC$_{50}$, the concentration of test compound which inhibits the specific binding by 50%, are determined.

The IC$_{50}$ values for the most active compounds are between 0.7 and 15 mM.

The compounds of the invention were also studied as regards their agonist or antagonist effects with respect to the 5-HT$_4$ receptors in rat oesophagus according to the method described by Baxter et al. in *Naunyn Schmied. Arch. Pharmacol.* (1991) 343 439.

Male Sprague-Dawley rats weighing 300 to 450 g are used. A fragment of about 1.5 cm of the terminal part of the oesophagus is removed rapidly, the muscle layer is removed, the internal muscular mucous tunic is opened longitudinally, it is mounted in an isolated-organ tank containing Krebs-Henseleit solution at 32° C. oxygenated by a stream of carbogen (95% O$_2$ and 5% CO$_2$), and is connected to an isometric transducer under a basal tension of 0.5 g. A contraction of the tissue is induced by the addition of 0.5 $\mu$M carbachol and, after waiting for the contraction to stabilize (15 min), the preparation is then exposed to serotonin (1 $\mu$M) in order to quantify the maximum relaxation. The tissue is washed and, after 20 min, a fresh 0.5 $\mu$m carbachol is added, and the preparation is exposed to the test compound at cumulative concentrations increasing from 0.1 to 1 $\mu$M. The compounds which induce a relaxation are considered as 5-HT$_4$ agonists.

For the compounds which do not induce relaxation, the preparation is exposed to serotonin at cumulative concentrations increasing from 0.1 nM to a concentration which induces a maximum relaxation, and the curve of relaxation due to serotonin, in the presence of the test compound, is then compared with a standard curve established in the absence of the said compound. If its presence induces a displacement of the curve towards the right, the test compound is then considered as a 5-HT$_4$ antagonist.

The results of these two biological tests show that the compounds of the invention are powerful ligands for the 5-HT$_4$-type serotoninergic receptors, and that they act on these receptors either as agonists or as antagonists.

The compounds can thus be used for the treatment and prevention of disorders in which the 5-HT$_4$ receptors are involved, whether this is at the level of the central nervous system, the gastrointestinal system, the cardiovascular system or the urinary system.

On the central nervous system, these disorders and complaints comprise, in particular, neurological and psychiatric disorders such as cognitive disorders, psychosis, compulsive and obsessive behaviour, depressive states and states of anxiety. The cognitive disorders comprise, for example, memory and attention deficiencies, dementia states (senile dementias such as Alzheimer's disease or age-related dementias), cerebrovascular deficiencies and Parkinson's disease. The psychoses comprise, for example, paranoia, schizophrenia, mania and autism. The compulsive and obsessive behaviour comprises, for example, eating disorders such as bulimia or loss of appetite. The depressive states and states of anxiety comprise, for example, anticipational-type anxiety (before a surgical operation, before dental treatment, etc.), anxiety caused by the dependence on or withdrawal from alcohol or drugs, mania, seasonally-induced disorders, migraine and nausea.

On the gastrointestinal system, these disorders and complaints comprise, in particular, vomiting induced by a medical treatment, direct or indirect disorders of gastromotility of the oesophagus, of the stomach or of the intestine, specific diseases such as dyspepsia, ulcers, gastro-oesophageal reflux, flatulence, irritable bowel syndrome, intestinal secretion disorders and diarrhoeas, for example those induced by cholera or by carcinoid syndrome.

On the cardiovascular system, these disorders and complaints comprise, in particular, pathologies associated, directly or indirectly, with cardiac arrhythmia.

On the urinary system, these disorders and complaints comprise, in particular, incontinence of any kind, as well as their causes or consequences, for example kidney damage, kidney stones or kidney infections.

The compounds of the invention can be in any composition form which is suitable for enteral or parenteral administration, such as tablets, coated tablets, gelatin capsules, wafer capsules, drinkable or injectable suspensions or solutions, such as syrups or vials, transdermal patches, suppositories, etc., combined with suitable excipients, and dosed to allow a daily administration of from 0.001 to 20 mg/kg.

What is claimed is:

1. Compound, optionally in the form of a pure optical isomer or a mixture of such isomers, corresponding to the general formula (I)

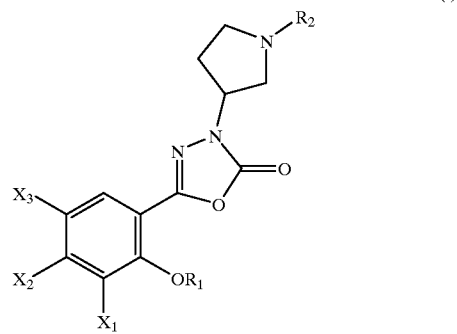

(I)

in which

R$_1$ represents a hydrogen atom or a (C$_1$–C$_4$)alkyl or cyclo(C$_3$–C$_7$)alkylmethyl group, X$_1$ represents a hydrogen or halogen atom or a (C$_1$–C$_4$) alkoxy group, or alternatively OR$_1$ and X$_1$ together represent a group of formula —OCH$_2$O—, —O(CH$_2$)$_2$—, —O(CH$_2$)$_3$—, —O(CH$_2$)$_2$O— or —O(CH$_2$)$_3$O—, X$_2$ represents a hydrogen atom, an amino group or a group of general formula —NHCO$_2$R in which R represents a (C$_1$–C$_4$)alkyl or phenyl(C$_1$—C$_2$)alkyl group, X$_3$ represents a hydrogen or halogen atom, and R$_2$ represents a hydrogen atom or a (C$_1$–C$_6$)alkyl group, or a phenyl(C$_1$–C$_4$)alkyl or [(4-dimethylamino)piperid-1-ylcarbonyl] (C$_2$–C$_4$) alkyl group, in the form of a base or an addition salt with an acid.

2. Process for the preparation of a compound according to claim 1, wherein an ester of general formula (II)

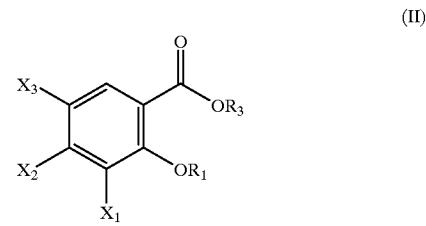

(II)

in which R$_1$, X$_1$, X$_2$ and X$_3$ are as defined in claim 1 and R$_3$ represents a methyl or ethyl group, is reacted with hydrazine hydrate, in order to obtain a hydrazide of general formula (III)

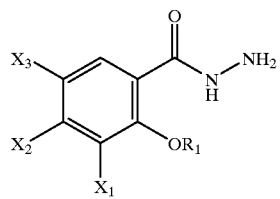

(III)

which is cyclized into an oxadiazole of general formula

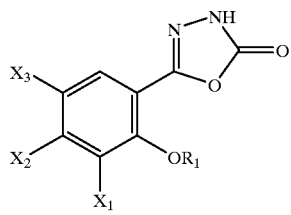

(IV)

either using phosgene, in an aprotic solvent, or using phenyl chloroformate, in an aprotic solvent, after which the oxadiazole of general formula (IV) is reacted with an alcohol of general formula (V)

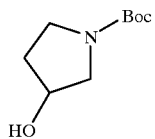

in which Boc represents a (1,1-dimethylethoxy)carbonyl group, in the presence of triphenylphosphine and ethyl azodicarboxylate, in an aprotic solvent, in order to obtain a compound of general formula (I) in which $R_2$ represents a hydrogen atom, and, finally, the latter compound is subjected to an alkylation using a derivative of general formula $R_2$-X, in which X represents a leaving group, and $R_2$ is as defined in claim 1, but is other than a hydrogen atom.

3. Pharmaceutical composition, which contains a compound according to claim 1, combined with an excipient.

4. A method for treating an amenable disorder in which a 5-$HT_4$ receptor is involved, which comprises administering an effective amount of a pharmaceutically acceptable compound according to claim 1 to a subject in need of such therapy.

5. A method for treating an amenable disorder in which a 5-$HT_4$ receptor is involved, which comprises administering an effective amount of a pharmaceutically acceptable compound according to claim 3 to a subject in need of such therapy.

* * * * *